(12) United States Patent
Hall

(10) Patent No.: US 11,857,286 B2
(45) Date of Patent: *Jan. 2, 2024

(54) DISPENSER AND FOLDED GLOVES SYSTEM AND METHOD

(71) Applicant: Sara R Hall, Cedar Park, TX (US)

(72) Inventor: Sara R Hall, Cedar Park, TX (US)

(*) Notice: Subject to any disclaimer, the term of this patent is extended or adjusted under 35 U.S.C. 154(b) by 5 days.

This patent is subject to a terminal disclaimer.

(21) Appl. No.: 17/508,546

(22) Filed: Oct. 22, 2021

(65) Prior Publication Data

US 2022/0039897 A1  Feb. 10, 2022

Related U.S. Application Data

(63) Continuation of application No. 16/827,052, filed on Mar. 23, 2020, now Pat. No. 11,154,376.

(51) Int. Cl.
*A61B 42/40* (2016.01)
*B65B 63/04* (2006.01)
*B65D 83/08* (2006.01)

(52) U.S. Cl.
CPC .............. *A61B 42/40* (2016.02); *B65B 63/04* (2013.01); *B65D 83/0805* (2013.01); *B65D 2583/08* (2013.01)

(58) Field of Classification Search
CPC .................................................. A61B 42/40
See application file for complete search history.

(56) References Cited

U.S. PATENT DOCUMENTS 11,154,376 B2 * 10/2021 Hall .................. B65D 83/0805

* cited by examiner

*Primary Examiner* — Gene O Crawford
*Assistant Examiner* — Ayodeji T Ojofeitimi
(74) *Attorney, Agent, or Firm* — The Langley Law Firm, P.C.

(57) ABSTRACT

A method includes opening a first cuff portion of a first glove, the first glove has the first cuff portion connected to a first palm portion and the first palm portion is connected to a first finger portion, and positing a second finger portion of a second glove into the first cuff portion of the first glove, the second glove includes the second finger portion connected to a second palm portion and the second palm portion is connected to a second cuff portion. The gloves are contained in a dispenser and the connection of finger into cuff allows for single glove removal in succession.

6 Claims, 6 Drawing Sheets

DISPENSER AND FOLDED GLOVES SYSTEM AND METHOD

CROSS-REFERENCE TO RELATED APPLICATIONS

The present application is a continuation and has benefit of priority of U.S. patent application Ser. No. 16/827,052, titled "Dispenser and Folded Gloves System and Method", filed Mar. 23, 2020, which prior application is co-pending and has at least one same inventor of the present application.

TECHNICAL FIELD

The invention generally relates to glove dispensing systems and methods, and more particularly relates to gloves and dispenser assemblies with particular methods of interweaving gloves for improved dispensing.

BACKGROUND

Gloves, such as nitrile, latex, vinyl, neoprene, rubber, and similar composition exam gloves, are widely employed in medical, laboratory, hospital, law enforcement, electronics, pharmaceutical, pesticide, chemical, craft, and other practices and activities. Spread of disease, for example, bacteria and viruses, can be hindered when gloves are worn to separate from body to body contact. Further, gloves can aid cleanliness by separating the wearer from chemicals, dirt, paints, microorganisms, blood, fluids, and the like.

Disposable glove use, in particular, is widespread and has given rise to a large industry of glove providers. Various conventional glove dispenser and glove arrangements are available. Typically, a glove user desires a pair of gloves. However, conventional dispensers and glove arrangement within the dispensers make it difficult to retrieve single gloves or glove pairs from single dispensing.

Others have attempted to provide gloves in dispensers where gloves are folded or interspersed in particular arrangements. Those arrangements, however, have been insufficient for retrieving single gloves and pairs of gloves from single dispensing. Often, excessive multiples of gloves fall from the dispenser when each single glove is sought. Also, the gloves of the dispenser may become embedded within the dispenser and not readily singly retrieved.

It would, therefore, be a significant improvement in the art and technology to provide glove and dispenser assemblies which provide for more easily removable gloves in desired quantity. It would further be an improvement to provide conventional gloves folded in a dispenser in manner to provide ready retrieval as desired by a glove wearer.

SUMMARY

An embodiment of the invention is a system including a first glove of a first finger portion, a first palm portion and a first cuff portion and a second glove of a second finger portion positioned in the first cuff portion of the first glove, a second palm portion and a second cuff portion.

Another embodiment of the invention is a method including opening a first cuff portion of a first glove, the first glove has the first cuff portion connected to a first palm portion and the first palm portion is connected to a first finger portion, and positing a second finger portion of a second glove into the first cuff portion of the first glove, the second glove includes the second finger portion connected to a second palm portion and the second palm portion is connected to a second cuff portion.

Yet another embodiment of the invention is a method of manufacture of a glove and dispenser assembly. The method of manufacture includes forming a succession of gloves each oriented with a respective finger portion of a next glove positioned in a cuff portion of a preceding glove of the succession, and folding each of the succession of gloves to direct a respective palm portion of the next glove towards the respective finger portion of the next glove.

BRIEF DESCRIPTION OF THE DRAWINGS

The present invention is illustrated by way of example and not limitation in the accompanying figures, in which like references indicate similar elements, and in which.

DETAILED DESCRIPTION

Figure 1:
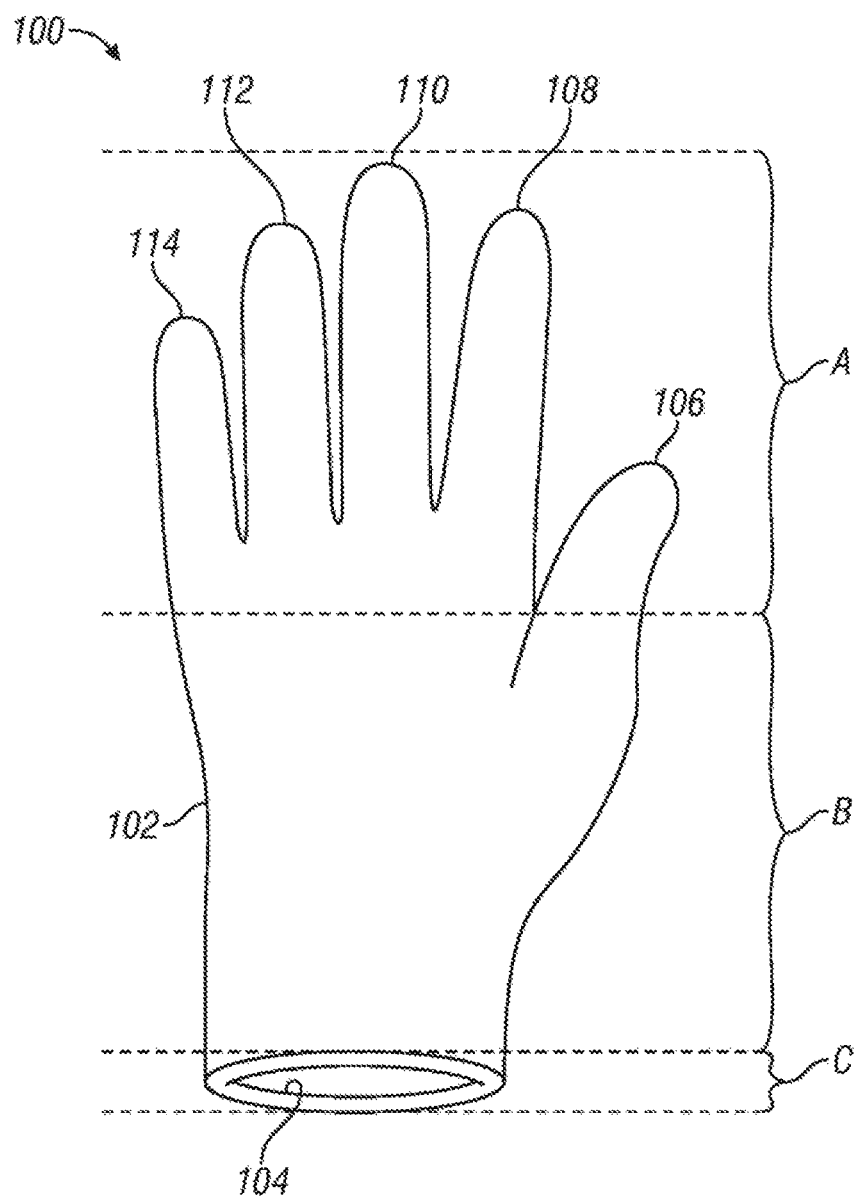
FIG. 1 illustrates a front perspective view of a glove of a finger portion, a palm portion and a cuff portion, according to certain embodiments of the invention.

Referring to FIG. 1, glove 100 includes a finger portion A, a palm portion B, and a cuff portion C. The finger portion A includes an index finger 108, a middle finger 110, a ring finger 112, and a pinky finger 114. A thumb finger 106 is also included in the glove, and may or may not be considered included in or as an aspect of the finger portion A in certain embodiments. In fact, the finger portion A may include any one or more fingers and/or thumb, as applicable in the embodiments. The palm portion B includes a generally cylindrical extension 102 from the finger portion A. The extension 102 opposing the finger portion A forms a cuff portion C. The cuff portion C is sized to accommodate insertion of a hand, the palm portion B is sized to accommodate a palm and back of the inserted hand, and the finger portion A is sized to accommodate respective pinky finger, ring finger, middle finger and index finger of the inserted hand in the pinky finger 114, ring finger 112, middle finger 110, and index finger 108, respectively, and thumb of the inserted hand in the thumb finger 106.

The glove 100 may be of any material and/or combination of materials. For non-exclusive example, the glove may be nitrile, latex, vinyl, neoprene, rubber, synthetic, fabric, composite, natural material, or otherwise. The glove 100 may be stretchable, twistable, gatherable, semi rigid, rigid, or otherwise or combinations of these. For non-exclusive example, same or different materials may form distinct or differentiated portions or parts of the glove 100. Additionally, the glove 100 may but need not include ribs, rolls, beading or other adornments or structures. Sizing of the glove 100 may depend on materials of construction, for non-exclusive example, the glove 100 may be of varied size, standard size, or combinations. If the glove 100 is for use in healthcare, law enforcement, industrial or laboratory applications, or otherwise, the glove may be of a standard or fixed length and width, and may be stretchable to fit tightly to a hand or else more loosely fit to the hand, as desired in the application. Although many variations of the glove 100 are possible in the embodiments, a particular non-exclusive type of the glove is a nitrile, latex, vinyl, neoprene or rubber glove that is stretched to accommodate the hand of a wearer.

Figure 2:
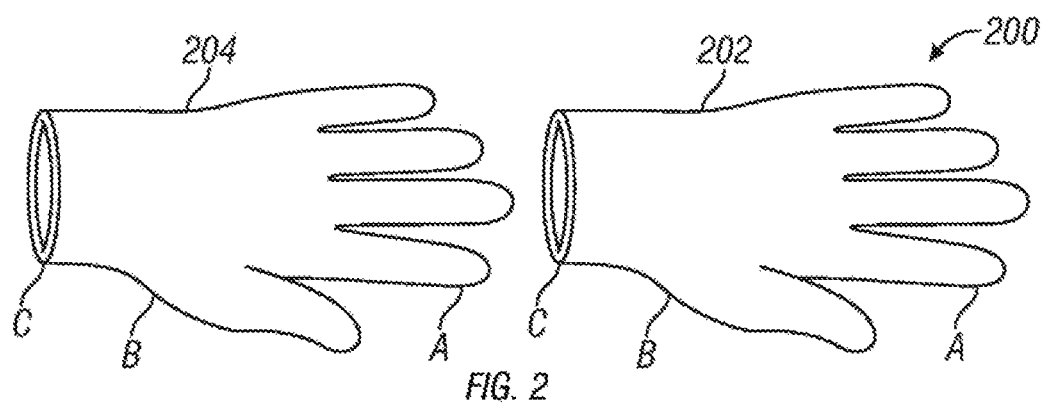
FIG. 2 illustrates a front perspective view of a first glove and a second glove oriented for insertion of fingers of the second glove into a cuff of the first glove, according to certain embodiments of the invention.

Referring to FIG. 2, in conjunction with FIG. 1, a pair 200 of gloves 202, 204 are each positioned aligned in sequence with the finger portion A (which finger portion A may include any one or more finger and/or the thumb, as applicable in the embodiment) of one glove 202 oriented away from the second glove 204 and with the cuff portion C of the glove 202 near the finger portion A of the second glove 204. The second glove 204 is oriented in sequential alignment from the first glove 202, such that the finger portion A of the second glove 204 is directed toward the cuff portion C of the first glove 202 and the cuff portion C of the second glove 204 is directed away from the first glove 202.

Figure 3:
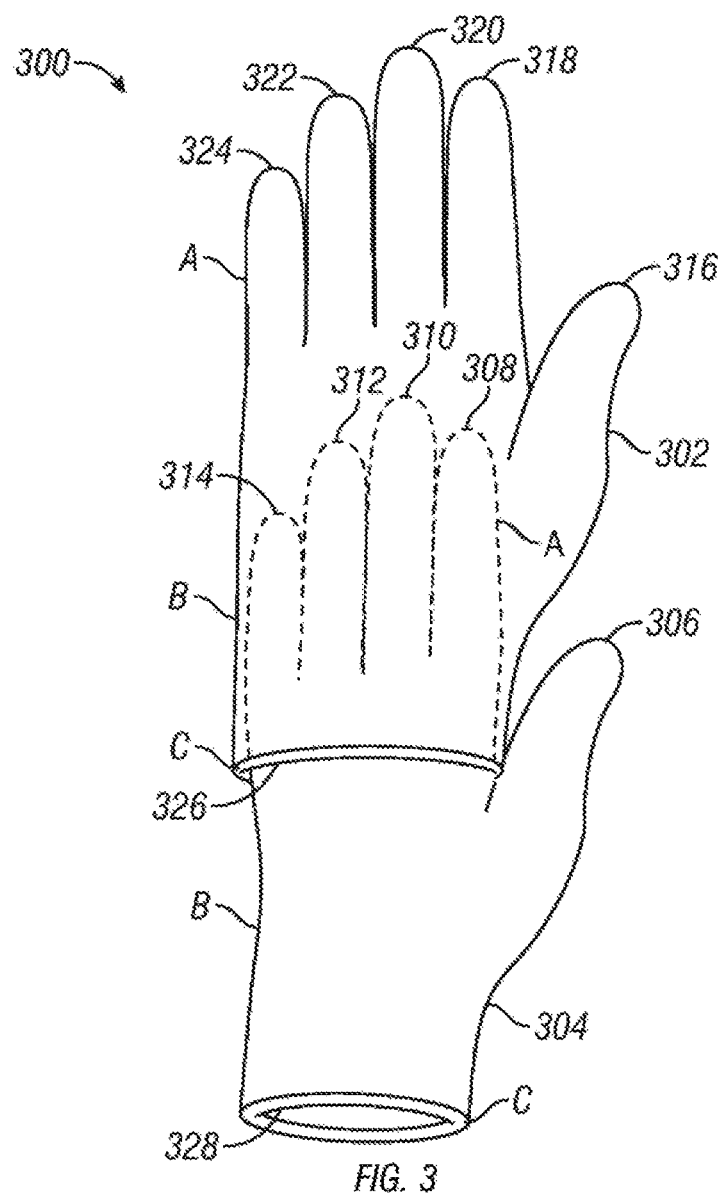
FIG. 3 illustrates a front perspective view of fingers of a second glove inserted into a cuff of a first glove, according to certain embodiments of the invention.

Referring to FIG. 3, in conjunction with FIGS. 1 and 2, a glove pair 300 includes glove 302 and glove 304. The gloves 302, 304 are manipulated such that a pinky finger 324, ring finger 322, middle finger 320 and index finger 318, as well as a thumb finger 316, of the glove 302 are spread away from the palm portion B of the glove 302 and the palm portion B is similarly extended to the cuff portion C of the glove 302. The glove 304 is positioned with a pinky finger 314, ring finger 312, middle finger 310, and index finger 308 of the glove 304 towards the cuff 326 of the glove 302. These fingers 314, 312, 310, 308 of the glove 304 are inserted into the cuff 326 of the glove 302. A thumb finger 306 of the glove 304 may extend outside the cuff 326 along extension of the glove 302, or else, according to certain embodiments, the thumb finger 306 may also be inserted in the cuff 326 or not. As inserted, a palm portion B of the glove 304 extends away from the cuff 326 of the glove 302 to form a cuff portion C of the glove 304. A cuff 328 is opened to receive fingers of another glove, as further described.

Figure 4:
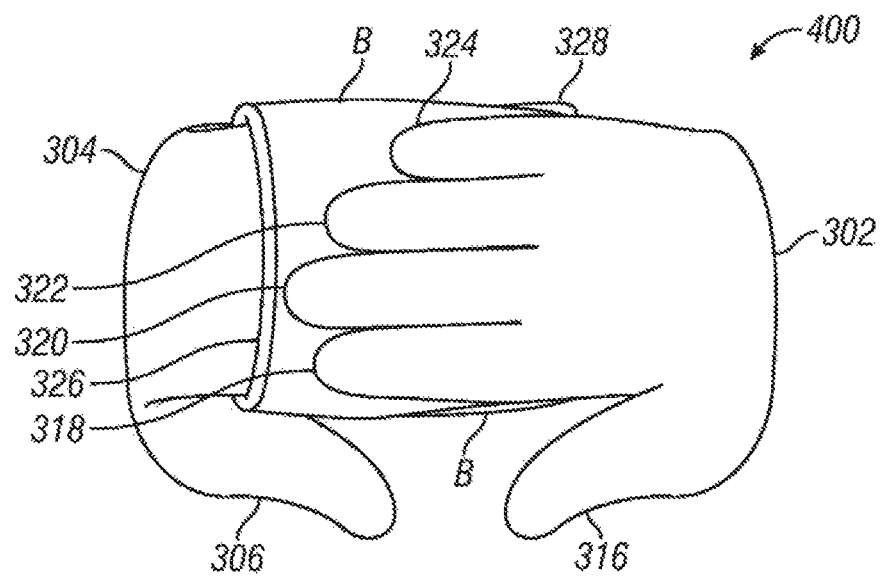
FIG. 4 illustrates a front perspective view of the second glove and first glove of FIG. 3, wherein fingers of the first glove are folded back toward a palm portion of the first glove and a palm portion of the second glove is folded back toward fingers of the second glove, according to certain embodiments of the invention.

Referring to FIG. 4, in conjunction with FIGS. 1, 2 and 3, packed gloves 400 include the glove 302 and the glove 304. The glove 302 is positioned with the pinky finger 324, the ring finger 322, the middle finger 320, and the index finger 318 folded against a first side of the palm portion B of the glove 302. (The thumb finger 316 may also be inserted or not, as applicable in the embodiments.) The inserted pinky finger 214, ring finger 312, middle finger 310 and index finger 308 (not shown) of the glove 304 remain within the cuff 326 of the glove 302. The palm portion B of the glove 304 is folded back against a second side of the palm portion B of the glove 302 opposite the first side. The thumb finger 316 of the glove 302 aligns along the palm portion B of the glove 302. The thumb finger 306 of the glove 304 aligns in opposite direction along the palm portion B of the glove 302.

Figure 5:
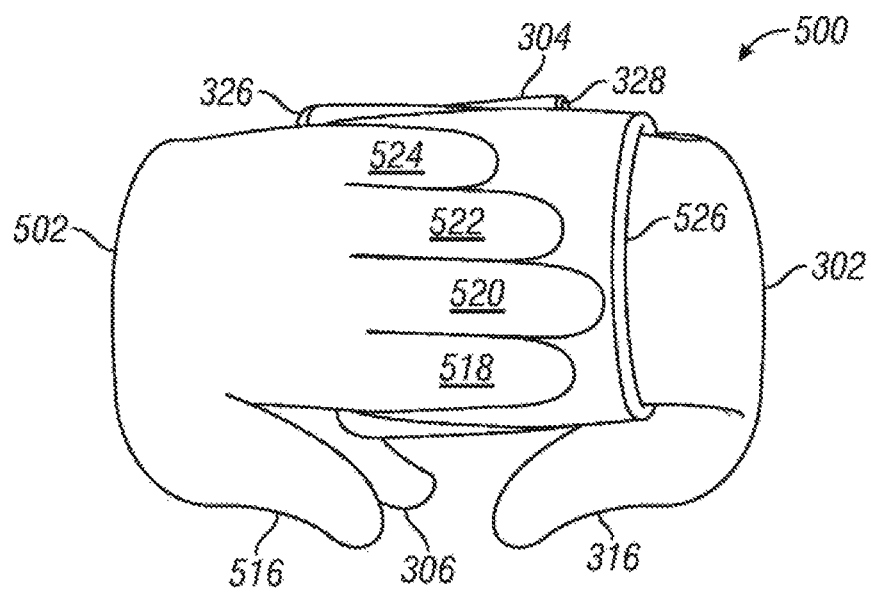
FIG. 5 illustrates a front perspective view of the first and second gloves of FIG. 4, and an additional third glove with fingers of the second glove inserted into a cuff portion of the third glove and a finger portion of the third glove folded back towards a palm portion of the third glove, according to certain embodiments of the invention.

Referring to FIG. 5, in conjunction with FIG. 4, another gloves set 500 include the packed gloves 400 and an additional glove 502. The pinky finger 324, ring finger 322, middle finger 320 and index finger 318 (not shown in FIG. 5 but shown in FIG. 4) are inserted into a cuff 526 of the glove 502. The glove 502 is folded, such that a pinky finger 524, ring finger 522, middle finger 520 and index finger 518 lie against a palm portion B of the glove 502. In certain embodiments, a thumb finger 516 of the glove 502 is positioned extending in same direction as the thumb finger 306 of the glove 304, alongside the palm portion B of the glove 502; although, according to other embodiments, the thumb finger 516 may also or alternatively be inserted in the cuff 526. As illustrated, successions of gloves are positioned with fingers (excluding thumb) of one glove within a cuff of another glove, in series from glove to glove.

Figure 6:
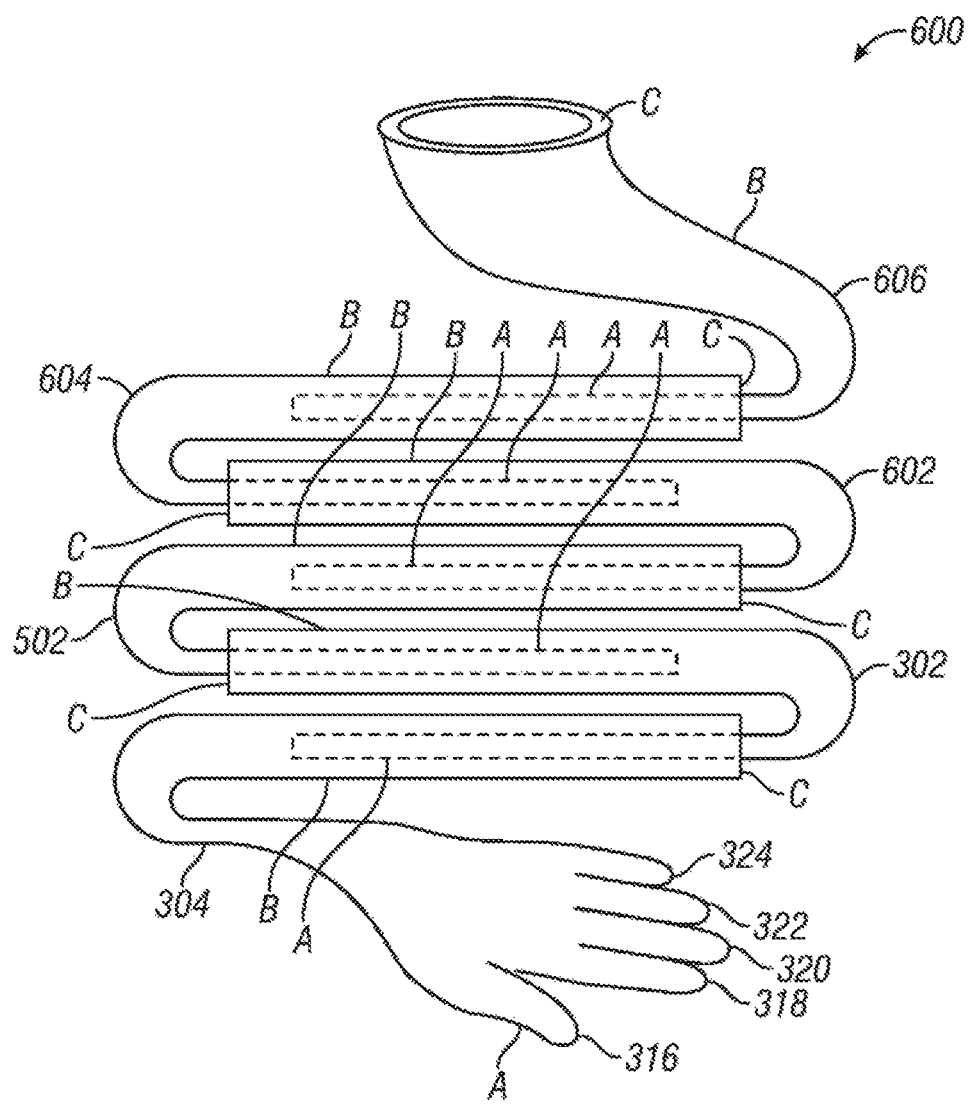
FIG. 6 illustrates a succession of gloves, each next successive glove has fingers inserted into a cuff of the preceding glove of the succession, according to certain embodiments of the invention.

Referring to FIG. 6, in conjunction with FIG. 5, a chain of gloves 600 adds other gloves 602, 604, 606 in succession, each with a respective finger portion A (which finger portion A may include any one or more fingers and/or thumb, as applicable in the embodiment) of a glove inserted into a cuff portion C of a next in succession glove. A respective palm portion B of each glove is folded back on the finger portion of the glove and contacts a respective palm portion B of a preceding in succession glove.

Figure 7:
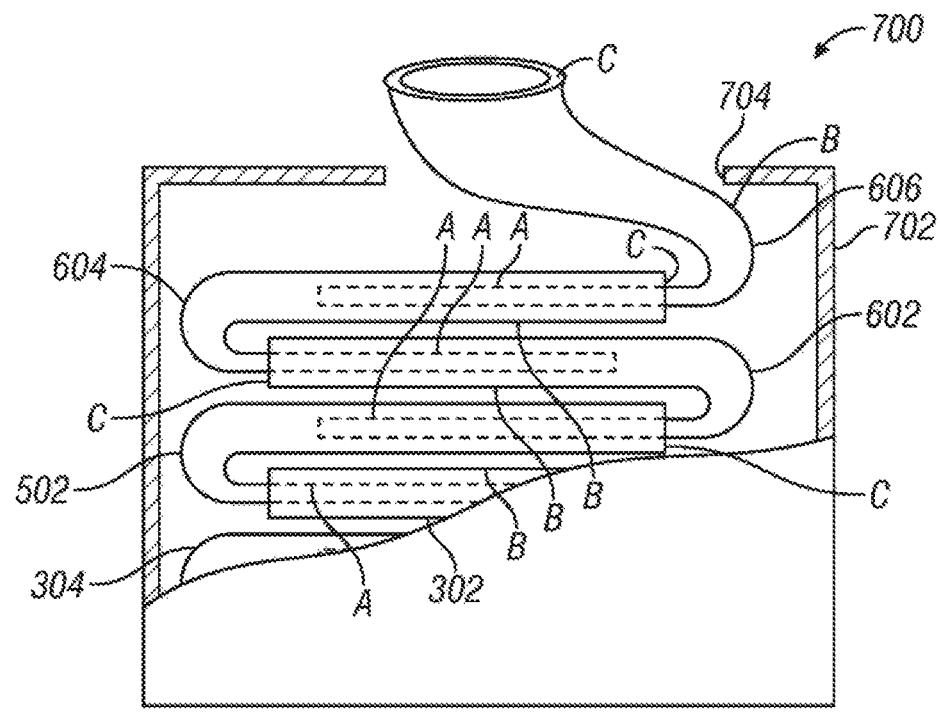
FIG. 7 illustrates a dispenser containing a succession of gloves, each next successive glove has fingers inserted into a cuff of the preceding glove of the succession, according to certain embodiments of the invention.

Referring to FIG. 7, in conjunction with FIG. 6, a glove dispenser 700 includes a container 702 formed with a hole 704. As non-exclusive example, the container 702 may be formed of paper, cardboard, plastic, metal or otherwise or combinations. The container 702 may be initially presented with the hole 704 closed, and the hole 704 may be formed, such as for non-exclusive example, by tearing a perforated line around the hole 704 or otherwise in the embodiments.

In any event, the chain of gloves 600 is positioned in the container 702 with a first glove 606 extending by a cuff portion C towards the hole 704. When the hole 704 is opened, the cuff portion C of the glove 606 may be pulled or otherwise presented to outward from the hole 704. Within the container 702, a succession of gloves 606, 604, 602, 502, 302, 304, etc. is retained. Each successive glove (bottom to top in the Figure) has a finger portion A (which finger portion A may include any one or more finger and/or thumb) positioned into a cuff portion C of a preceding glove. The gloves may be positioned in any manner within the container 702, such as for non-exclusive example, the gloves may each be folded with a palm portion B folded back towards a finger portion A of the same glove, or other arrangements of gloves are possible. In any event, the positioning of the fingers of one glove within the cuff of a preceding glove in succession, permits retrieval from the hole 704 of each next glove without simultaneous retrieval of a next in succession glove in the series.

Figure 8:
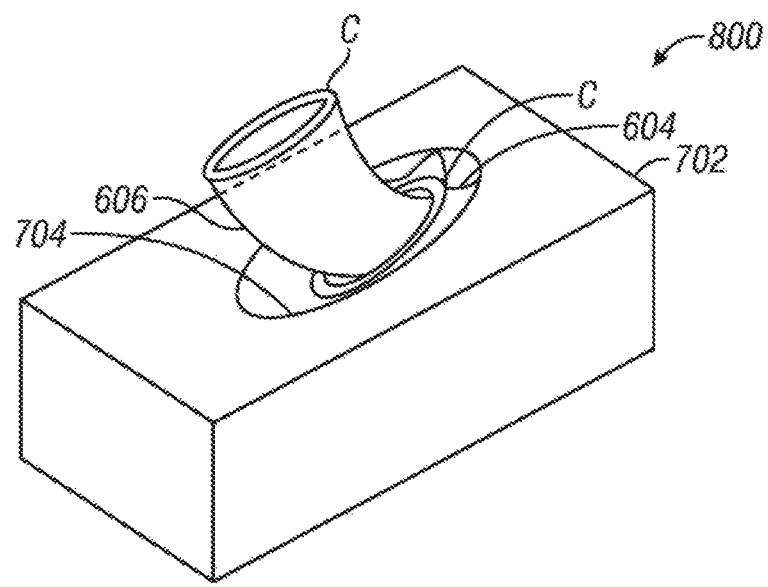
FIG. 8 illustrates a dispenser containing a succession of gloves, wherein each next successive glove has fingers inserted into a cuff of the preceding glove of the succession in manner to allow for single retrieval of gloves in order of succession, according to certain embodiments of the invention.

Referring to FIG. 8, in conjunction with FIG. 7, a glove and dispenser assembly 800 includes the container 702 formed with the hole 704. Gloves contained in succession, with at least some fingers of each glove inserted into cuff of next glove in succession, are retrievable singly from hole 704. Because of the particular interconnection of fingers of one glove inside the cuff of another glove, the gloves are singly retrieved by cuff portion from the container 702.

Figure 9:
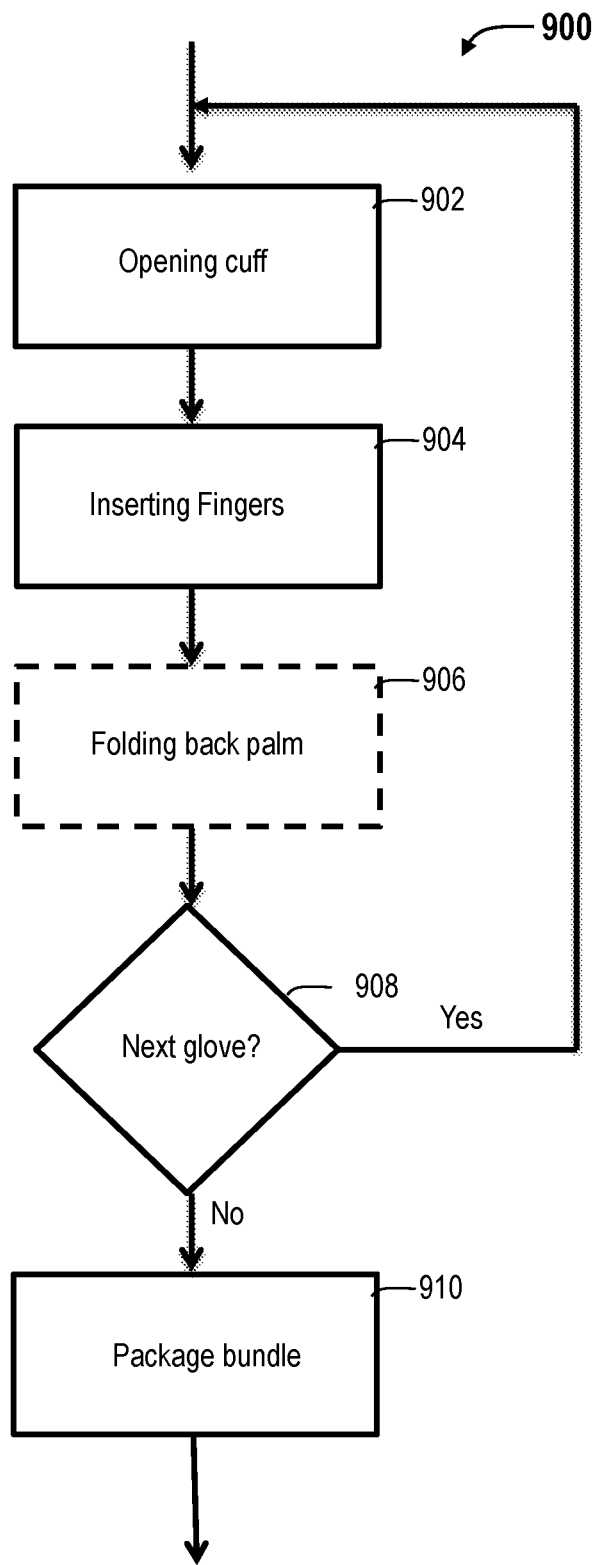
FIG. 9 illustrates a method of connecting a succession of gloves for single glove dispensing and method of manufacture of such gloves for a dispenser, according to certain embodiments of the invention.

Referring to FIG. 9, a method 900 of a glove and dispenser assembly includes opening 902 a cuff of a first glove. A finger portion (which can include any one or more finger and/or thumb) of a second glove is inserted 904 into the opened cuff of the first glove. Although not necessary in all embodiments, a palm portion of second glove is folded back 906 towards the finger portion of the second glove. The method 900 proceeds with repeating steps 902 and 904, and if included 906, for each successive glove of a plurality of gloves for a dispenser container.

When the last glove of the plurality is encountered, and steps 902 and 904 (and if applicable, 906) are performed for the glove, the interconnected gloves of the plurality are packaged in a dispenser, such as for non-exclusive example, the container 702.

In the foregoing, the invention has been described with reference to specific embodiments. One of ordinary skill in the art will appreciate, however, that various modifications, substitutions, deletions, and additions can be made without departing from the scope of the invention. Accordingly, the specification and figures are to be regarded in an illustrative rather than a restrictive sense, and all such modifications substitutions, deletions, and additions are intended to be included within the scope of the invention. Any benefits, advantages, or solutions to problems that may have been described above with regard to specific embodiments, as well as device(s), connection(s), step(s) and element(s) that may cause any benefit, advantage, or solution to occur or become more pronounced, are not to be construed as a critical, required, or essential feature or element.

What is claimed is:

1. A system, comprising:
   a first glove of a first finger portion, a first palm portion and a first cuff portion;
   a second glove of a second finger portion positioned in the first cuff portion of the first glove, a second palm portion and a second cuff portion.

2. A combination glove dispenser and plurality of gloves, comprising:
   a container for containing a glove bundle including a first glove of a first finger portion, a first palm portion and a first cuff portion and a second glove of a second finger portion positioned in the first cuff portion of the first glove, a second palm portion and a second cuff portion.

3. The system of claim 2, further comprising:
   a third glove of a third finger portion position in the second cuff portion of the second glove, a third palm portion and a third cuff portion.

4. The system of claim 3, wherein the container includes an opening from which the third cuff portion of the third glove is readily accessible to retrieve the third glove and thereby position the second cuff portion for next retrieval from the container.

5. A method of manufacture of a glove and dispenser assembly, comprising:
   forming a succession of gloves each oriented with a respective finger portion of a next glove positioned in a cuff portion of a preceding glove of the succession; and
   folding each of the succession of gloves to direct a respective palm portion of the next glove towards the respective finger portion of the next glove.

6. The method of manufacture of claim 5, further comprising:
   packing the succession of gloves from forming and folding in a container about a length and a width of each glove of the succession of gloves.

\* \* \* \* \*